Figure 1:

United States Patent [19]

Holjevac et al.

[11] Patent Number: 5,252,481
[45] Date of Patent: Oct. 12, 1993

[54] MUTANT OF BACTERIUM *CLOSTRIDIUM HISTOLYTICUM*, A PROCESS FOR THE OBTAINING THEREOF, AND ITS USE IN THE PRODUCTION OF CLOSTRIPAIN-FREE COLLAGENASE

[75] Inventors: Milan Holjevac; Ivan Udovicic; Sonja Cizmek; Vlasta Sojak-Derkos; Stjepan Gamulin; Vladimir Delic, all of Zagreb, Yugoslavia

[73] Assignee: Pliva Farmaceutska, Kemijska, Yugoslavia

[21] Appl. No.: 733,764

[22] Filed: Jul. 23, 1991

[30] Foreign Application Priority Data

Jul. 23, 1990 [YU] Yugoslavia ............................. 1440/90

[51] Int. Cl.$^5$ ........................ C12N 1/20; C12N 9/00; C12N 9/52
[52] U.S. Cl. ................. 435/252.7; 435/220; 435/183; 435/842
[58] Field of Search ..................... 435/252.7, 183, 220, 435/842, 183, 252.7, 842, 220

[56] References Cited

U.S. PATENT DOCUMENTS 3,201,325 8/1965 Barton .................................. 435/220
3,677,900 7/1972 Merkel ................................. 435/220
3,705,083 12/1972 Chiulli et al. ....................... 435/220
3,821,364 6/1974 Chiulli et al. ....................... 435/220

OTHER PUBLICATIONS

Merck Index, 11th Edition, 1989, p. 1396 #8684 Soybean.
Emod, I. et al., Five sepharose bound ligands for the chromatog. pur. of *Clostridium collagenase & clostripain* (see abstract); 1977, 77/1 (51–56).

*Primary Examiner*—Douglas W. Robinson
*Assistant Examiner*—Deborah K. Ware
*Attorney, Agent, or Firm*—Pollock, Vande Sande & Priddy

[57] ABSTRACT

A mutant of bacterium *Clostridium histolyticum*, designated *Clostridum histolyticum* K26 clo 88 of the following characteristics: the lack of a motility system which is a fundamental characteristic of the parenteral strain; and, the inability to biosynthesize the accompanying enzyme clostripain. A process of obtaining the above mutant and its use in a process for the production of clostripain-free collagenase are also provided.

7 Claims, 1 Drawing Sheet

MUTANT OF BACTERIUM *CLOSTRIDIUM HISTOLYTICUM*, A PROCESS FOR THE OBTAINING THEREOF, AND ITS USE IN THE PRODUCTION OF CLOSTRIPAIN-FREE COLLAGENASE

This invention relates to a novel mutant of bacterium *Clostridium histolyticum*, to a process for the obtaining thereof by means of a chemical mutagenic agent, and to its use in an improved process for the production of clostripain-free collagenase (clostridiopeptidase A).

It is well known that the enzyme collagenase is used not only for scientific purposes but also finds its place in human and veterinary therapy, in particular for the treatment of skin disorders. In combination with some non-specific proteases it accelerates the process of wound healing by removing necrotic tissue and consequently, by improving epithelization. Collagenase is also used in surgery in cases of tissue transplantation and for tissue disintegration.

In human medicine collagenase is used in the therapy of burns of different degrees, decubitus, skin ulcers, crusts, etc. Epithelization and recovery of the skin by means of collagenase, in addition to being more efficient and rapid, also prevents the formation of keloids and hydertrophic growth as a result of formed collagen disintegration under the action of collagenase. Various species of microorganisms cultivated under defined conditions are known to synthesize collagenase.

In the course of collagenase purification process the accompanying enzyme clostripain causes great difficulties since its chemical and physical properties are very similar to those of collagenase. Medicinal preparations do not contain clostripain.

Maschman, E.O. (Biochem, Z., 297, 284, 1938) was the first to describe collagenase obtained by cultivation of bacterium *Clostridium perfringens*. Among all organisms which synthesize collagenase, *Clostridium histolyticum* was found to be the best producer. MacLennan, J.D., Piandi, 1. and Howes, E.I. (J. Clin. Inv., 32, 1317, 1953) have described the conditions for growth of *Clostridium histolyticum*. They investigated the composition of liquid medium which consisted mostly of proteose-peptone, inorganic salts and vitamin solution. Bacterium was cultivated at a temperature of 370° C. and at pH 7.2. Berman, S., Lowenthal, J P., Webster, M.E., Altieri, P.L. and Gochenour, E.B. (J. Bact., 82, 5829 1961) also performed investigations of the conditions for growth of *Clostridium histolyticum* with the aim of producing collagenase. They succeeded in cultivating *Clostridium histolyticum* in a nutrient medium containing no inorganic salts but only proteose-peptone, enzymatically hydrolized proteins of casein and soy (tryptic soy broth) and vitamin solution. Such composition of nutrient medium also conditioned other values required for satisfactory bacterial growth and biosyrthesis of collagenase, such as pH value of 8.5 and temperature of 30° C.

Lettl, A. (J.Hyg.Epidemiol.Microbio.Immunol., 18, (4)47, 1974) succeeded in substituting proteose-peptone with other hydrolized proteins in the composition of nutrient medium used for cultivation of Clostridium, histolyticum.

*Clostridium histolyticum* is an anaerobic bacterium and for its cultivation in a liquid medium anaerobic conditions must be secured. Takahashi, S. and Seifert, S. (J.Appl.Bact., 35, 47, 1972) used in their investigations the reducing agents sodium thioglycolate and sodium bisulfite to obtain anaerobic conditions needed for bacterial growth. Optimal results, i.e. the highest collagenase yield was obtained when the mentioned reducing agents were used in a 1:1 ratio.

Chiulli, A.J. and Wegman E.H. (U.S. Pat. No. 3,705,083) described the production of collagenase by cultivation of a mutant of *Clostridium histolyticum* which showed improved properties relative to lower toxicity compared to parenteral toxicity and a possibility of inhibiting growth of other bacteria. Bacterium *Clostridium histolyticum* recovers in the medium the enzyme collagenase together with greater amounts of other active extracellular proteases (non-specific proteases, alpha-toxin, accompanying brown pigment), in particular clostripain (clostridiopeptidase B). Thus, it has been found that commercially available preparations contain traces of clostripain (Keil, B., Mol.Cell Biochem., 23, 87, 1979). Difficulties are encountered in the course of purification process and individual isolation from fermentation medium due to very, similar chemical and physical properties of these proteases.

Bacterium *Clostridium histolyticum* cultivated under known anaerobic submerged conditions in a medium containing conventional sources of carbon, nitrogen, mineral salts and vitamin solutions, at a temperature of 32°–370° C. and at pH range of 7.2–8.8, over a period of 10–24 hours secretes in the medium the enzyme collagenase (clostridiodeptase A), clostripain (clostridiopeptidase B) and other non-specific proteases. The problems encountered in such enzyme production consist in the presence of both enzymes, collagenase and clostripain in the filtrate. In the course of collagenase separation from clostripain, a large portion of collagenase is lost, resulting in reduced enzyme yield and consequently, increased costs per product unit.

We have now surprisingly found that the use of a novel mutant of bacterium *Clostridium histolyticum* in the production of collagenase solves all the aforesaid problems.

Hence, one object of the present invention is a novel mutant of bacterium

Clostridium histolyticum, designated *Clostridium histolyticum* K-26 clō 88, which was deposited:

i) at the Institute of Biochemical Engineering, Laboratory of Microbiology, Zagreb, Pierottijeva 6, on May 22, 1990, under the accession number 4043, ii) and in conformance with the Budapest Treaty on the International Recognition of the Deposit of Microorganisms for the Purposes of Patent Procedure, pursuant to Rule 7.1, at the National Collection of Agricultural and Industrial Microorganisms, Department of Microbiology and Biotechnology, University of Horticulture and Food Industry, Somloi ut 14–16, H-1118 Budapest, Hungary on June 4, 1991, under the accession number NCAIM B (P) 001 145.

A further object of the present invention is a process of obtaining said novel mutant *Clostridium histolyticum* K-26 clō 88, by treating spores of Clostridium histolyticum K-26 (deposited at the Institute of Biochemical Engineering, Laboratory of Microbiology, Zagreb, Pierottijeva 6, on May 22, 1990, under the accession number 4042) with the mutagenic agent N-methyl-N'-nitro-N-nitrosoguanidine for 45 and 90 minutes at about room temperature, whereupon the spores are separated by centrifugation, suspended in a physiological solution, inoculated into a solid medium, and incubated at 37° C. for about 3 days under amaerobic conditions.

Figure 2:

The novel mutant *Clostridium histolyticum* K-26 clō 88 of the present invention differs from the parental strain *Clostridium histolyticum* K-26 in two essential characteristics. As, it can be seen from FIGS. 1 and 2 (enclosed) obtained by electron micrography, the mutant has lost its motility system which is a fundamental characteristic of the parenteral strain classified according to Bergey's Manual of Systematic Bacteriology (Sneath, P.H.A., Mair, N.S., Scharpe, F.E., Holt, J.G.; Eds:Williams and Wilking, Baltimore, London, Los Angeles, Sidney, Vol.2, 1170, In distinction to the parenteral strain the second new characteristic of the novel mutant consists in its inability to biosynthesize the accompanying enzyme clostripain. This property was discovered by means of immunological precipitation reaction of anticlostripain and anticollagenase serum with mutant cultivation filtrates, as well as by method of analysis described in following text.

Each grown colony is tested for enzyme biosynthesis by both biochemical analysis and immuno-precipitation test. Presence or absence of clostripain is determined on the basis of appearance of a precipitation line between the filtrate of *Clostridium histolytlicum* K-26 culture and rabbit anticlostripain serum.

A further object of the present invention is a process for the production of clostripain-free collagenase, wherein said novel mutant *Clostridium histolyticum* K-26 clō 88 is cultivated in a nutrient medium containing proteose-peptone, enzymatically hydrolyzed proteins of casein and soy (tryptic soy broth), a vitamin solution, e.g. riboflavin, nicotinamide, pyridoxine, panthothenic acid, a reducing agent, e.g. Na-thioglycolate, and inorganic salts, if required, e.g. NaHPO$_4$, mgSO$_4$, FeSO$_4$, for 10 to 24 hours, at a temperature ranging from 28° to 37° C. and a pH of 7.2 to 8.9, tinder anaerobic submersed conditions. During cultivation the enzyme collagenase recovers in liquid medium. The product is clostripain-free. Cultivation is followed by purification and isolation. The collagenase yield is increased by approx. 10 to 20% in comparison to usual methods for collagenase production. Activity of obtained collagenase was determined by applying the method after Gassman, V. and Nordwig, A. (Hoppe-Seyler's Z. Phys. Chem., 322, 267, 1960) with synthetic substrate.

Clostripain activity was determined using a modified method described in the catalogue of the firm Worthington, 1987, p.47.

Procedure for non-specific proteolytic activity determination was derived from the definition of casein activity unit in compliance with the catalogue of the firm Sigma, 1990, p.333. For incubation and precipitation were applied common conditions required for proteolytic activity determination. Determination of released amino groups was carried out, according to a modified colorimetric ninhydrin method after Rosen, H. (Arch. Biochem.Biochys. , 67, 10, 1957).

In order to maintain the activity of collagenase during possible freezing and lyophilization, liquid enzyme preparation is treated by adding carbohydrates, such as saccharose, maltose or the like, at concentrations ranging from $5 \times 10^{-3}$ M to $2.5 \times 10^{-2}$ M. For stabilization of activity of lyophilized collagenase preparation soluble proteins are added (enzymatically hydrolized casein (Fluka), Peptone I in powder form (Torlak), acid hydrolized casein (Serva), etc.) at concentrations ranging from 10 to 50 mg/mL of liquid enzyme preparation.

This invention is illustrated by the following examples:

EXAMPLE 1

The spores of *Clostridium histolyticum* K-26 are treated with 3 mg/mL of N-methyl-N'-nitro-N-nitrosoguanidine (MNNG) dissolved in 10 ml- of TRIS buffer for 45 and 90 minutes. Mutagenic MNNG is removed by centrifugation and decantation of supernatant. The spores are suspended in a physiological solution, inoculated on agar medium in an adequate dilution and incubated under anaerobic conditions at 370° C. for 3 days.

The colonies grown in a solid medium are inoculated into liquid nutrient medium and after two days of growth at 370° C. the culture is pipetted into a well, 8 mm in diameter. In another adjacent well of the same size, placed at 2 cm distance, rabbit anticlostripain serum is pipetted. Gel diffusion of clostripain antibodies and clostripain leads to their linkage and formation of a precipitation line. In this way each mutant is controlled several times in addition to biochemical assay. Absence of precipitation line is an evidence that mutants are not producing clostripain. Obtained mutants are then lyophilized and stored for further use.

EXAMPLE 2

Lyophilized parenteral strain K-26 of the bacterium *Clostridium histolyticum* was used for inoculation of pre-fermentation nutrient medium containing the following:

| | |
|---|---|
| proteose-peptone | 50 g/L |
| tryptic soy broth | 15 g/L |
| Na$_2$HPO$_4$ | 9 g/L |
| MgSO$_4 \times$ 7H$_2$O | 0.08 g/L |
| FeSO$_4 \times$ 7H$_2$O | 0.014 g/L |
| vitamin solution | 5 mL/L |
| vitamin solution: | |
| pantothenic acid | 200 mg/L |
| nicotinamide | 200 mg/L |
| pyridoxine | 200 mg/L |
| thiamine HCl | 200 mg/L |
| riboflavin | 20 mg/L |

Used medium had a natural pH value. Sterilization was performed at 1200° C. for 30 minutes, whilst vitamin solution was sterilized at 1150° C. for 15 minutes. Immediately prior to inoculation of medium with microorganism the solution of vitamins was added. The microorganism was. cultivated for a period of 20 hours at a temperature of 37° C. in a stationary way.

The second stage of bacterium cultivation was performed in a 2 Lit glass bioreactor (Multigene, New Brunswick, N.Y.) under the following conditions: 1500 mL of medium of the same composition as the pre-fermentation medium, but with addition of 10% of inoculum and with pH value of 7.4 and a temperature of 30° C. The fermentation was conducted for 20 hours, under occasional nitrogen bubbling conditions for the purposes of anaerobiosis and mild mixing at 50 rpm.

| Enzyme yield: | |
|---|---|
| collagenase | 1.32 U/mL |
| clostripain | 3.0 U/mL |
| non-specific proteases | 820 U/mL |

EXAMPLE 3

In this example the parenteral strain K-26 of *Clostridium histolyticum* was used for inoculation of pre-fermentation nutrient medium (as in Example 2). After 20 hours of cultivation 10% of this inoculum was used for inoculation of a nutrient medium of the following composition:

| | |
|---|---|
| proteose-peptone | 50 g/L |
| tryptic soy broth | 15 g/L |
| vitamin solution | 5 mL/L |
| Na-thioglycolate | 0.57 g/L |

Composition of vitamin solution was identical to that described in Example 2 with pH value 7.4. Medium was sterilized at 1200° C. for 30 min and cultivation was performed in a 2-Lit glass bioreactor (Multigene, New Brunswick, N.Y.) with 1500 mT of described medium, at a temperature of 370° C. for 7 hours.

| Enzyme yield: | |
|---|---|
| collagenase | 1.32 U/mL |
| clostripain | 2.02 U/mL |
| non-specific proteases | 790 U/mL |

EXAMPLE 4

This example relates to the use of the lyophilized mutant of *Clostridium histolyticum* K-26 clō 88, obtained as described in Example 1, for inoculation of pre-fermentation medium of the composition and cultivation conditions as described in Example 2. Ten percent of inoculum was used for inoculation of liquid medium. The fermentation was conducted for 7 hours.

| Enzyme yield: | |
|---|---|
| collagenase | 1.2 U/mL |
| clostripain | 0.0 U/mL |
| non-specific proteases | 630 U/mL |

EXAMPLE 5

This example relates to the use of the lyophilized mutant of *Clostridium histolyticum* K-26 clō 88, obtained as described in Example 1, which was inoculated into a nutrient medium of the composition as described in Example 3. Cultivation of aforementioned bacterium was performed at 28° C. for 8–10 hours.

| Enzyme yield: | |
|---|---|
| collagenase | 2.72 U/mL |
| clostripain | 0.0 U/mL |
| non-specific proteases | 466 U/mL |

EXAMPLE 6

Lyophilized mutant of *Clostridium histolyticum* K-26 clō 88, obtained as described in Example 1, was used in this example as an inoculum for pre-fermentation medium as described in this Example 2. Cultivated microorganism was used as an inoculum for the second stage of fermentation as described in Example 3. The only difference was the pH value of 8.7 and a temperature of 30° C. Cultivation was interrupted after 10 hours.

| Enzyme yield: | |
|---|---|
| collagenase | 4.4 U/mL |
| clostripain | 0.0 U/mL |
| non-specific proteases | 376 U/mL |

EXAMPLE 7

This example shows the procedure of enzyme isolation from a sterile ultrafiltrate of fermentation medium of the mutant *Clostridium histolyticum* K-26 clō 88 which does not produce clostripain. Concentrated culture filtrate, obtained as described in Examples 4, 5 and 6, was treated with 0.03–0.05 M of calcium chloride and acetone at the concentrations of 18–33%. Fractional precipitation was achieved by adding ammonium sulphate first to 20–30% saturation and then to 70–80% saturation and finally, by a two-stage treatment with calcium phosphate gel, whilst treatment with acetone was omitted. Active lyophilized, clostripain-free collagenase preparation was obtained with utilization amounting to 75–85%.

| Enzyme yield: | |
|---|---|
| collagenase | 2.2 U/mg |
| clostripain | 0.0 U/mg |
| non-specific proteases | 45 U/mg |

EXAMPLE 8

This example shows the procedure of collagenase isolation from a sterile ultrafiltrate of fermentation medium of the mutant *Clostridium histolyticum* K-26 clō 88, obtained as described in Examples 4, 5 and 6 and treated as indicated in Example 7, but by avoiding treatment with ammonium sulphate to 30% saturation. A white active, lyophilized collagenase preparation, clostripain-free, was obtained with utilization ranging between 75 and 90%.

| Enzyme yield: | |
|---|---|
| collagenase | 2.5 U/mg |
| clostripain | 0.0 U/mg |
| non-specific proteases | 45 U/mg |

EXAMPLE 9

This example shows the procedure of collagenase isolation from samples obtained as described in Examples 4, 5 and 6, and purified in a way described in Examples 7 and 8, but by avoiding treatment with calcium phosphate gel. A white, lyophilized, clostripain-free collagenase preparation was obtained with utilization ranging between 75 and 90%.

| Enzyme yield: | |
|---|---|
| collagenase | 2.6 U/mg |
| clostripain | 0.0 U/mg |
| non-specific proteases | 44 U/mg |

EXAMPLE 10

This example illustrates a method for purification of liquid product obtained by cultivation and treatment as described in Examples 3 and 7. The purification procedure consists in the application of sample to the column containing Sephadex G-75. Application to the column and eluation of protein fractions was performed with buffer 0.01 11 TRIS HC1 at pH 7.2 and with addition of 0.01 M calcium acetate. Gel filtration procedure enabled identification of three protein fractions. Analysis confirmed collagenase activity in the first fraction, reduced collagenase activity in the second, whilst in the third fraction brown pigment was identified, in addition to activity of non-specific proteases, as follows:

| I fraction | |
|---|---|
| collagenase | 34.2 U/mL |
| clostripain | 0.0 U/mL |
| non-specific proteases | 0.0 U/mL |
| II fraction | |
| collagenase | 10.5 U/mL |
| clostripain | 0.0 U/mL |
| non-specific proteases | 0.0 U/mL |
| III fraction | |
| collagenase | 0.0 U/mL |
| clostripain | 0.0 U/mL |
| non-specific proteases | 535 U/mL |

EXAMPLE 11

This example describes the desalination process of samples of purified collagenase fractions. Liquid ultrafiltrated fractions of pure enzyme obtained as described in Example 10 were taken and applied to the column containing Sephadex G-25. Sample application and eluation were performed using distilled water. One fraction of salt-free pure enzyme was obtained. Activity of pure enzyme was 38.2 U/mL.

EXAMPLE 12

This example refers to preservation of collagenase activity in liquid preparation during freezing and lyophilization. The following procedure was employed to a liquid preparation obtained as described in Examples 7-11 carbohydrates were added, such as for example saccharose, maltose and the like, in the concentrations ranging from $5 \times 10^{-3}$ M to $2.5 \times 10^{-2}$ M.

EXAMPLE 13

This example describes the ways by which it is possible to stabilize lyophilized collagenase preparation. The procedure consists in adding to liquid collagenase preparation, obtained as described in Examples 7-11, different soluble proteins such as enzymatically hydrolized casein (Fluka), Pepton 1 in powder form (Torlak), acid hydrolized casein (Serva) and others, in concentrations ranging from 10 to 50 mg/ml of liquid enzyme preparation. Thus, lyophilized collagenase-preparation shows its unchanged activity.

What we claim is:

1. A biologically pure, non-motile culture of *Clostridum histolyticum*, NCAIM B(P) 001145, which produces clostripain-free collagenase.

2. A process of obtaining a biologically pure, non-motile culture of *Clostridium histolyticum*, NCAIM B(P) 001145 which produces clostripain-free collagenase wherein said process comprises treating spores of said *Clostridium histolyticum* NACIM B(P) 001145 with the mutagenic agent, N-methyl-N'-nitro-N-nitrosoguanidine, for 45 to 90 minutes, at about room temperature, then separating the spores by centrifugation, suspending the spores in a physiological solution, inoculating the spores into a solid medium, and incubating at 37 degrees for about 3 days under anaerobic conditions to obtain said strain.

3. A process for the production of clostripain-free collagenase, which comprises cultivating *Clostridium histolyticum* NCAIM B(P) 001145 in a liquid nutrient medium containing proteose-peptone, enzymatically hydrolyzed proteins of casein and soy, a vitamin solution, a reducing agent, and nitrogen, for 10 to 24 hours at a temperature ranging from 28 degrees celsius to 37 degrees celsius and a pH of 7.2 to 8.9, under anaerobic submersed conditions, and with a combination of precipitants isolating purified clostripain-free collagenase.

4. The process of claim 3 which further comprises stabilizing said purified clostripain-free collagenase by adding to said purified collagenase, carbohydrate in a concentration ranging from $5 \times 10^{-3}$ M to $2.5 \times 10^{-2}$ M and soluble protein in a concentration of 10 to 50 mg/ml of said purified collagenase.

5. The process of claim 3 wherein said vitamin solution contains riboflavin.

6. The process of claim 3 wherein said reducing agent is Na-thioglycolate.

7. The process of claim 5 wherein said combination of precipitants contains calcium chloride, acetone, ammonium sulfate and calcium phosphate gel.

* * * * *

UNITED STATES PATENT AND TRADEMARK OFFICE
CERTIFICATE OF CORRECTION

PATENT NO. : 5,252,481  Page 1 of 2
DATED : October 12, 1993
INVENTOR(S) : Holjevac, et al.

It is certified that error appears in the above-identified patent and that said Letters Patent is hereby corrected as shown below:

Column 1, line 27, change "hvdertrophic" to ---hypertrophic---.
Column 1, line 41, change "Piandi, 1." to ---Mandl, I---.
Column 1, line 46, change "370°" to ---37°---.
Column 1, line 48, change "F.B." to ---R.B.---.
Column 1, line 54, change "hvdrolized" to ---hydrolized---.
Column 1, line 57, change "biosyr-" to ---biosyn---.
Column 1, line 63, change "Clostridium" to ---Clostridium---.
Column 1, line 64, change "histolyticum" to ---histolyticum---.
Column 2, line 28, change "370°" to ---37°---.
Column 2, line 42, after "bacterium" insert ---Clostridium histolyticum---.
Column 2, line 43, delete "Clostridium histolyticum"
Column 2, line 61, please take out the bold number 88 and type the in regular print.
Column 2, line 61, change "Clostridium histolyticum" to ---Clostridium histolyticum---.
Column 3, line 2, change "amaerobic" to ---anaerobic---.
Column 3, line 13, change "1170," to ---1170, 1986)---.
Column 3, line 25, change "histolytlicum" to ---histolyticum---.
Column 3, line 35, change "mg" to ---Mg---.
Column 3, line 37, change "tinder" to ---under---.
Column 3, line 45, change "Gassman, V." to ---Grassman, L.W.---.
Column 3, line 46, change "Chem." to ---Chim.---
Column 3, line 58, change "bioshys." to ---Biophys.---
Column 4, line 5, change "K" to ---K---.
Column 4, line 12, change "370°" to ---37°---.
Column 4, line 16, change "370°" to ---37°---.
Column 4, line 28, change "parenteral" to ---parental---.
Column 4, line 47, change "1200°" to ---120°---.
Colume 4, line 48, change "1150°" to ---115°---.
Column 5, line 3, change "parenteral" to ---parental---.

UNITED STATES PATENT AND TRADEMARK OFFICE
CERTIFICATE OF CORRECTION

PATENT NO. : 5,252,481
DATED : October 12, 1993
INVENTOR(S) : Holjevac, et al.

It is certified that error appears in the above-identified patent and that said Letters Patent is hereby corrected as shown below:

```
Column 5, line 18, change "1200°" to ---120°---.
Column 5, line 20, change "mT" to ---mL---.
Column 5, line 21, change "370°" to ---37°---.
Column 7, line 5, change "ll TRIS HCl" to ---M TRIS HCl---.
Column 8, line 6, change "mg/ml" to ---mg/mL---.
Column 8, line 17, change "NACIM" to ---NCAIM---.
Column 8, line 39, change "mg/ml" to ---mg/mL---.
```

Signed and Sealed this

Sixteenth Day of August, 1994

Attest:

BRUCE LEHMAN

*Attesting Officer*     *Commissioner of Patents and Trademarks*